US00PP33906P3

(12) United States Plant Patent
Schoone

(10) Patent No.: US PP33,906 P3
(45) Date of Patent: Jan. 25, 2022

(54) ***PHALAENOPSIS* PLANT NAMED 'SANDMAN'**

(50) Latin Name: *Phalaenopsis hybrida*
Varietal Denomination: Sandman

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/339,975

(22) Filed: Jun. 5, 2021

(65) Prior Publication Data

US 2021/0385999 P1 Dec. 9, 2021

Related U.S. Application Data

(60) Provisional application No. 62/705,003, filed on Jun. 6, 2020.

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ... A01H 5/02; A01H 5/00; A01H 5/08; A01H 6/62
See application file for complete search history.

*Primary Examiner* — June Hwu
(74) *Attorney, Agent, or Firm* — C. Anne Whealy

(57) ABSTRACT

A new and distinct cultivar of *Phalaenopsis* plant named 'Sandman', characterized by its relatively compact and upright plant habit; moderately vigorous growth habit; strong flowering stems; strong leaves; freely flowering habit with typically two inflorescences per plant, each inflorescence with numerous flowers; pale yellow-colored flowers with radiating purplish red-colored dashes and spots; and good postproduction longevity.

2 Drawing Sheets

Figure 1:
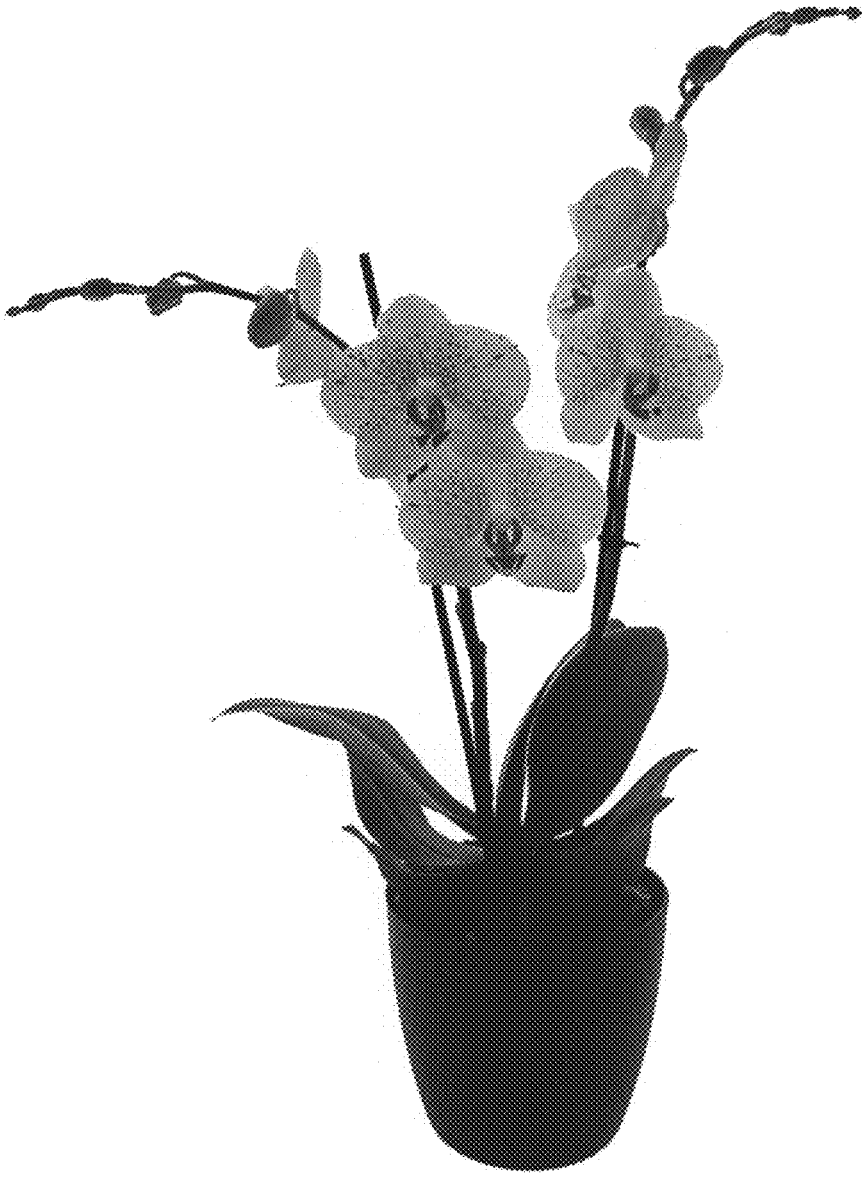

Botanical designation: *Phalaenopsis hybrida.*
Cultivar denomination: 'SANDMAN'.

CROSS-REFERENCED TO CLOSELY-RELATED APPLICATIONS

Title: Varieties of *Phalaenopsis* Plants
Inventor: René Schoone
Filed: Jun. 6, 2020
Ser. No.: 62/705,003
Inventor and Applicant/Assignee hereby claims the benefit of this provisional U.S. Patent Application.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B.V. of Heemskerk, The Netherlands on Mar. 18, 2021, application number 2021/0836. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Sandman'.

The new *Phalaenopsis* plant is a product of a planned breeding program conducted by the Inventor in De Lier and Heemskerk, The Netherlands. The objective of the breeding program is to develop new fast-growing and freely flowering *Phalaenopsis* plants with good leaf shape and large flowers with unique and attractive patterns and coloration.

The new *Phalaenopsis* plant originated from a cross-pollination in April, 2009 in Nantou, Taiwan of *Phalaenopsis hybrida* 'Diamond Beauty', not patented, as the female, or seed, parent with *Phalaenopsis hybrida* 'Nankung's 4.55 PM', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in February, 2018.

Asexual reproduction of the new *Phalaenopsis* plant by in vitro meristem propagation in a controlled environment in Assendelft, The Netherlands since February, 2019 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sandman'. These characteristics in combination distinguish 'Sandman' as a new and distinct *Phalaenopsis* plant:

1. Relatively compact and upright plant habit.
2. Moderately vigorous growth habit.
3. Strong flowering stems.
4. Strong leaves.
5. Freely flowering habit with typically two inflorescences per plant, each inflorescence with numerous flowers.
6. Pale yellow-colored flowers with radiating purplish red-colored dashes and spots.
7. Good postproduction longevity.

Plants of the new *Phalaenopsis* can be compared to plants of the female parent, 'Diamond Beauty'. Plants of the new *Phalaenopsis* differ primarily from plants of 'Diamond Beauty' in flower color as flowers of plants of the new *Phalaenopsis* are pale yellow in color with purplish red-colored dashes and spots whereas flowers of plants of 'Diamond Beauty' are dark yellow in color with only a few spots and no dashes or stripes. In addition, flower labella of plants of the new *Phaleanopsis* have cirrose tips whereas flower labella of plants of 'Diamond Beauty' do not develop cirrose tips.

Plants of the new *Phalaenopsis* can be compared to plants of the male parent, 'Nankung's 4.55 PM'. Plants of the new *Phalaenopsis* differ primarily from plants of 'Nankung's 4.55 PM' in flower color as flowers of plants of the new *Phalaenopsis* are pale yellow in color with purplish red-colored dashes and spots whereas flowers of plants of 'Nankung's 4.55 PM' are white in color with only a few spots and no dashes or stripes.

Plants of the new *Phalaenopsis* can be compared to plants of *Phalaenopsis hybrida* 'Florida Sun', not patented. In side-by-side comparisons, plants of the new *Phalaenopsis* differ primarily from plants of 'Florida Sun' in plant habit as plants of the new *Phalaenopsis* are more compact than plants of 'Florida Sun'. In addition, flowers of plants of the new *Phalaenopsis* have fewer spots than flowers of plants of 'Florida Sun'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Sandman' grown in a container.

Figure 2:
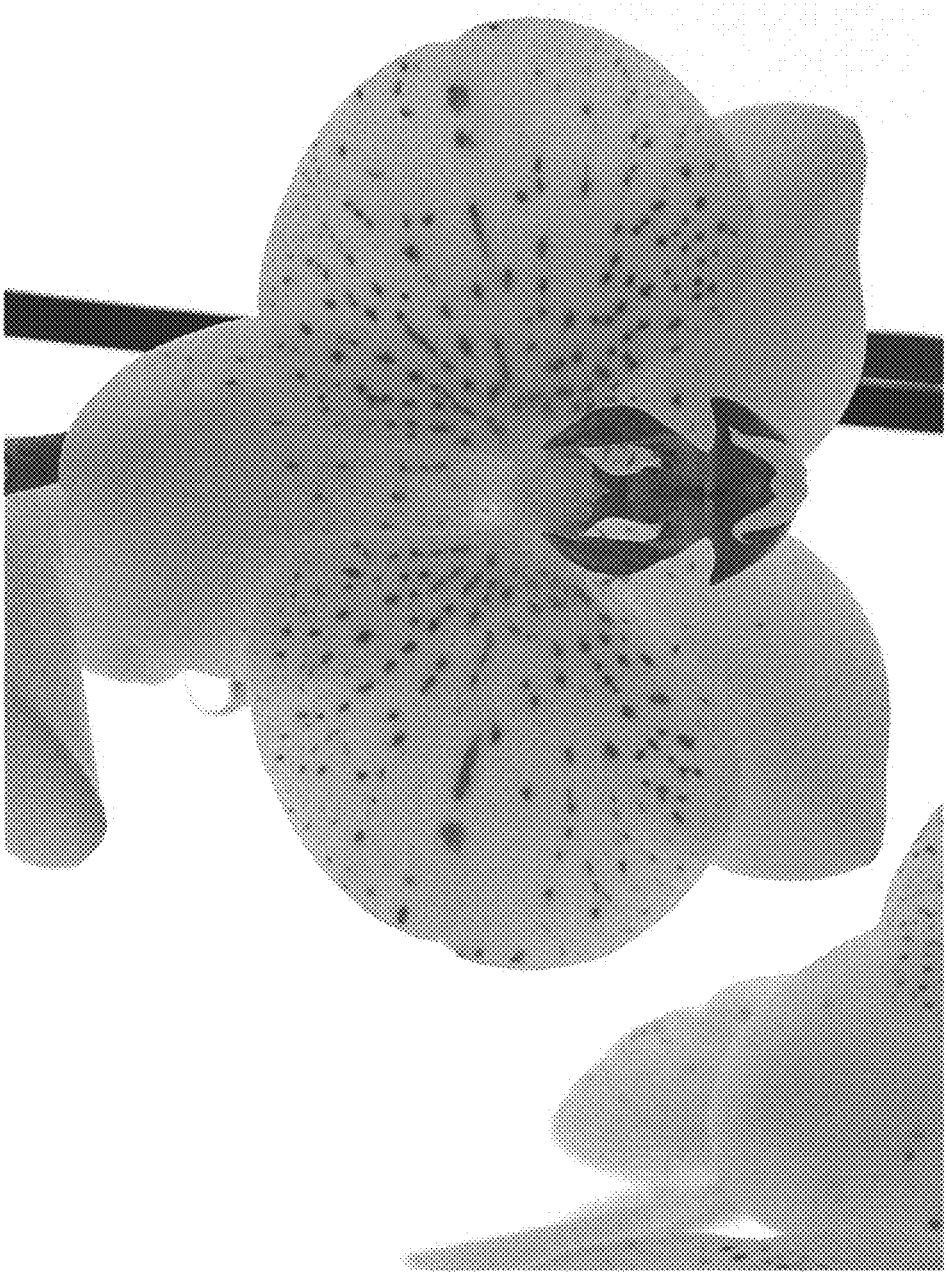

The photograph on the second sheet (FIG. 2) is a close-up view of a typical flower of 'Sandman'.

DETAILED BOTANICAL DESCRIPTION

The aforementioned photographs and following observations and measurements describe plants grown during the early spring in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Sandman'.

Parentage:

*Female parent.*—*Phalaenopsis hybrida* 'Diamond Beauty', not patented.

*Male parent.*—*Phalaenopsis hybrida* 'Nankung's 4.55 PM', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thick, fibrous; typically grey to green in color; actual color of the roots is dependent on substrate composition, water quality, fertilizer, substrate temperature and age of roots.

*Rooting habit.*—Low amount of branching; medium density.

Plant description:

*Plant form and growth habit.*—Herbaceous epiphyte; relatively compact and upright plant habit with typically two inflorescences per plant, each inflorescence with numerous flowers; monopodial; moderately vigorous growth habit and moderate growth rate.

*Plant height, substrate level to top of foliar plane.*—About 13.5 cm.

*Plant height, substrate level to top of inflorescences.*—About 35.8 cm.

*Plant diameter or spread.*—About 26.1 cm.

Leaf description:

*Arrangement and quantity.*—Distichous, simple; sessile; about five leaves per plant.

*Length.*—About 16 cm.

*Width.*—About 6.2 cm.

*Aspect.*—Upright to outwardly arching.

*Shape.*—Oblanceolate to narrowly elliptic; slightly carinate.

*Apex.*—Unequal acute.

*Base.*—Sheathing. Sheath length: About 1.3 cm. Sheath width: About 1.2 cm. Sheath color: Close to 146C to 146D.

*Margin.*—Entire; slightly revolute.

*Texture and luster, upper and lower surfaces.*—Smooth, glabrous; slightly glossy.

*Venation pattern.*—Camptodromous.

*Color.*—Developing leaves, upper surface: Close to 146A. Developing leaves, lower surface: Close to 146A to 146B; towards the margins, tinged with close to 200B to 200C. Fully expanded leaves, upper surface: Close to 146B; venation, close to 146A.

Fully expanded leaves, lower surface: Close to 146B; margin edges, close to 146C; venation, close to 144A.

Inflorescence description:

*Appearance and flowering habit*.—Showy zygomorphic flowers arranged on axillary branched racemes; typically two inflorescences per plant; each inflorescence with about ten flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 26.1 cm.

*Inflorescence width*.—About 12.5 cm.

*Flower buds*.—Height: About 1.8 cm. Diameter: About 1.2 cm by 1.4 cm. Shape: Broadly ovate. Color: Upper surface, close to 144B; lower surface, close to 144C.

*Flower size*.—About 7.4 cm (vertical) by 8.1 cm (horizontal).

*Flower depth*.—About 3 cm.

*Petals, quantity and arrangement*.—Three, two lateral petals and one center petal transformed into a labellum.

*Lateral petals*.—Length: About 4.1 cm. Width: About 4.6 cm. Shape: Reniform. Apex: Retuse. Margin: Entire. Texture and luster, upper and lower surfaces: Smooth, glabrous, velvety; matte. Color: When opening, upper surface: Close to 150D with radiating dashes and spots along veins, close to 59B. When opening, lower surface: Close to a blend of 150D and 154D with radiating dashes and spots along veins, close to 181D. Fully opened, upper surface: Close to 157C with radiating dashes and spots along veins, close to 60D. Fully opened, lower surface: Close to 157B to 157C with radiating dashes and spots along veins, close to 186C to 186D.

*Labella*.—Appearance: Three-parted with two lateral lobes and a central lobe. Length, lateral lobes: About 1.6 cm. Width, lateral lobes: About 7 mm. Length, central lobe: About 2.9 cm. Width, central lobe: About 6 mm to 17 mm. Shape, lateral lobes: Narrowly obovate. Shape, central lobe: Narrowly rhomboid. Apex, lateral lobes: Obtuse. Apex, central lobe: Cleft with two narrow and strongly recurved cirrose tips, about 1.1 cm in length and about 8 mm in width. Margins, lateral lobes: Entire; convex. Margins, central lobe: Entire. Texture and luster, upper and lower surfaces: Smooth, glabrous, moderately velvety; matte. Callosities: Located at the base of the labellum and attachment point of the lateral petals; about 4 mm in length, about 5 mm in width and about 5 mm in height. Color: When opening, upper surface: Lateral lobes: Ground color, close to 155B; distally, close to 59B and 59C and proximally, 156D tinged with close to 12B and marbled with close to 166B to 166C. Central lobe: Close to 60A; towards the apex, close to 72B and at the apex, close to NN155D; basal margin, close to 165D and at the base (at column connection) close to 161D with stripes, close to 70A; main vein, close to 165D; cirrose tips, close to NN155D. Callosities: Close to 14B; fine dots, close to 28A. When opening, lower surface: Lateral lobes: Close to 157A and 162D; towards the apex, close to 64B and apical margin, close to 164A. Central lobe: Close to NN155B; towards the center, close to 166C; towards the apex, close to 161B and apical margin, close to 70B; at the base; at the base (at column connection) close to 156D. Fully opened, upper surface: Lateral lobes: Ground color, close to NN155B; distally, close to 71B and 71D and proximally, tinged with close to 12B and marbled with close to 178B and 178C. Central lobe: Close to 60A; towards the apex, close to 72B and at the apex, close to NN155D; basal margin, close to 165D and at the base (at column connection) close to 161D with stripes, close to 70A; main vein, close to 165D; cirrose tips, close to NN155D. Callosities: Close to 14B; fine dots, close to N25A. Fully opened, lower surface: Lateral lobes: Close to N155A; towards the apex, close to 64B and apical margin, close to 166B. Central lobe: Close to NN155B; towards the center, close to 165C; towards the apex, close to 161B and apical margin, close to 70B; at the base; at the base (at column connection) close to 157D.

*Sepals*.—Quantity and arrangement: Three, one upper dorsal sepal and two lower lateral sepals. Length, dorsal sepal: About 4.4 cm. Width, dorsal sepal: About 3.5 cm. Length, lateral sepals: About 4.3 cm. Width, lateral sepals: About 3.2 cm. Shape, dorsal sepal: Broadly ovate to broadly elliptic. Shape, lateral sepals: Ovate. Apex, dorsal sepal: Retuse to shallowly emarginate. Apex, lateral sepals: Bluntly acute. Base, dorsal and lateral sepals: Truncate. Margin, dorsal sepal: Entire. Margin, lateral sepals: Entire; basal margins, coarsely undulate. Texture and luster, dorsal and lateral sepals, upper and lower surfaces: Smooth, glabrous, velvety; matte. Color, dorsal sepal: When opening, upper surface: Close to a blend of 145C and 145D with radiating dashes and spots along veins, close to 59B. When opening, lower surface: Close to a blend of 145C and 150C; towards the apex, close to 150B; radiating dashes and spots along veins, close to 181D. Fully opened, upper surface: Close to 157A; towards the margins and apex, close to 157D; proximally, radiating dashes and spots along veins, close to 60C to 60D. Fully opened, lower surface: Close to 150D with radiating dashes and spots along veins, close to 181D. Color, lateral sepals: When opening, upper surface: Close to 145C with radiating dashes and spots along veins, close to 59B. When opening, lower surface: Close to a blend of 145C and 150C; towards the apex, close to 150B; radiating dashes and spots along veins, close to 181D. Fully opened, upper surface: Close to 145D; towards the lower margin, close to 157A; proximally, radiating dashes and spots along veins, close to 60C to 60D. Fully opened, lower surface: Close to 145D with radiating dashes and spots along veins, close to 181D; main vein, distally, close to 145C.

*Peduncles*.—Length: About 40.6 cm. Diameter: About 6 mm. Strength: Strong. Aspect: Upright to outwardly arching. Texture and luster: Smooth, glabrous; matte. Color: Close to 138B, densely covered with fine dots, close to 197A.

*Pedicels*.—Length: About 3.1 cm. Diameter: About 3 mm. Strength: Moderately strong. Aspect: About 50° from peduncle axis. Texture and luster: Smooth, glabrous; matte. Color: Close to 150D; proximally, close to 144A.

*Reproductive organs*.—Androecium: Column length: About 9 mm. Column width: About 6 mm. Column color: Close to NN155B. Pollinia quantity: Two. Pollinia diameter (per two pollinia): About 2.5 mm. Pollinia color: Close to 17A. Gynoecium: Stigma length: About 3 mm. Stigma width: About 4.5 mm. Stigma shape: Reniform. Stigma color: Close to NN155C. Ovary length: About 1.1 cm. Ovary diameter: About 1 mm. Ovary color: Close to 150D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 15° to about 40° C. and are suitable for USDA Hardiness Zones 10 to 12.

It is claimed:

1. A new and distinct *Phalaenopsis* plant named 'Sandman' as illustrated and described.

* * * * *